(12) United States Patent
Arneson et al.

(10) Patent No.: US 9,480,459 B2
(45) Date of Patent: Nov. 1, 2016

(54) ULTRASOUND SCANNING CAPSULE ENDOSCOPE

(71) Applicant: INNURVATION, INC., Columbia, MD (US)

(72) Inventors: Michael Arneson, Finksburg, MD (US); William Bandy, Gambrills, MD (US); Wayne Shanks, Baltimore, MD (US)

(73) Assignee: Innurvation, Inc., Glen Burnie, MD (US)

( * ) Notice: Subject to any disclaimer, the term of this patent is extended or adjusted under 35 U.S.C. 154(b) by 28 days.

(21) Appl. No.: 14/147,124

(22) Filed: Jan. 3, 2014

(65) Prior Publication Data

US 2014/0323867 A1    Oct. 30, 2014

Related U.S. Application Data

(63) Continuation of application No. 13/073,424, filed on Mar. 28, 2011, now Pat. No. 8,647,259.

(60) Provisional application No. 61/318,012, filed on Mar. 26, 2010.

(51) Int. Cl.
| | |
|---|---|
| *A61B 8/14* | (2006.01) |
| *A61B 8/12* | (2006.01) |
| *A61B 8/00* | (2006.01) |
| *G01S 7/00* | (2006.01) |

(Continued)

(52) U.S. Cl.
CPC .............. *A61B 8/12* (2013.01); *A61B 8/4488* (2013.01); *G01S 7/003* (2013.01); *G01S 7/52017* (2013.01); *G01S 7/52065* (2013.01); *G01S 15/8915* (2013.01)

(58) Field of Classification Search
CPC ... A61B 8/12; A61B 8/4488; G01S 15/8915; G01S 7/52065; G01S 7/003; G01S 7/52017
USPC ................................................ 600/437–469
See application file for complete search history.

(56) References Cited

U.S. PATENT DOCUMENTS

| | | |
|---|---|---|
| 2,788,390 A | 4/1957 | Sheldon |
| 2,987,960 A | 6/1961 | Sheldon |
| 3,329,074 A | 7/1967 | Gosselin |

(Continued)

FOREIGN PATENT DOCUMENTS

| | | |
|---|---|---|
| EP | 1326432 A2 | 7/2003 |
| EP | 1492352 A2 | 12/2004 |

(Continued)

*Primary Examiner* — Sanjay Cattungal
(74) *Attorney, Agent, or Firm* — Sterne, Kessler, Goldstein & Fox P.L.L.C.

(57) ABSTRACT

The present invention relates to ultrasound imaging on a capsule endoscope platform. It relates to the generation of a focused ultrasound acoustic signal and the receiving of echo signals from the wall of a body lumen with an array of acoustic transducers wrapped around the circumference of the capsule. It relates to sending the generated echo image signals to receiver devices attached or worn on the body. It relates to the generation of 360° overlapping sidewall ultrasound scans of a body lumen, and image processing techniques to assemble these scans into a high resolution continuous ultrasound image. Finally, it relates to the manufacture and assembly of such an ultrasound scanning capsule endoscope (USCE). The concept is extendable to conventional endoscopes and catheters.

26 Claims, 16 Drawing Sheets

(51) Int. Cl.
*G01S 7/52* (2006.01)
*G01S 15/89* (2006.01)

(56) References Cited

U.S. PATENT DOCUMENTS

| | | | |
|---|---|---|---|
| 3,608,547 A | 9/1971 | Sato et al. | |
| 3,730,175 A | 5/1973 | Fukami et al. | |
| 4,987,897 A | 1/1991 | Funke | |
| 5,010,412 A | 4/1991 | Garriss | |
| 5,131,398 A | 7/1992 | Alfano et al. | |
| 5,251,326 A | 10/1993 | Silverman | |
| 5,265,033 A | 11/1993 | Vajk et al. | |
| 5,267,033 A | 11/1993 | Hoshino | |
| 5,279,607 A | 1/1994 | Schentag et al. | |
| 5,329,498 A | 7/1994 | Greenstein | |
| 5,559,757 A | 9/1996 | Catipovic et al. | |
| 5,575,290 A * | 11/1996 | Teo et al. | 600/456 |
| 5,604,531 A | 2/1997 | Iddan et al. | |
| 5,741,311 A | 4/1998 | Mc Venes et al. | |
| 5,744,898 A | 4/1998 | Smith et al. | |
| 5,796,827 A | 8/1998 | Coppersmith et al. | |
| 5,833,603 A | 11/1998 | Kovacs et al. | |
| 5,993,378 A * | 11/1999 | Lemelson | 600/109 |
| D457,236 S | 5/2002 | Meron et al. | |
| D457,621 S | 5/2002 | Meron et al. | |
| D457,948 S | 5/2002 | Meron et al. | |
| D464,425 S | 10/2002 | Meron et al. | |
| D469,864 S | 2/2003 | Meron et al. | |
| 6,607,301 B1 | 8/2003 | Glukhovsky et al. | |
| 6,628,989 B1 | 9/2003 | Penner et al. | |
| 6,632,171 B2 | 10/2003 | Iddan et al. | |
| 6,702,755 B1 | 3/2004 | Stasz et al. | |
| 6,720,709 B2 | 4/2004 | Porat et al. | |
| D492,403 S | 6/2004 | Iddan et al. | |
| 6,754,472 B1 | 6/2004 | Williams et al. | |
| 6,764,446 B2 | 7/2004 | Wolinsky et al. | |
| 6,836,377 B1 | 12/2004 | Kislev et al. | |
| 6,845,190 B1 | 1/2005 | Smithwick et al. | |
| 6,847,844 B2 | 1/2005 | Sun et al. | |
| 6,855,111 B2 | 2/2005 | Yokoi et al. | |
| 6,856,712 B2 | 2/2005 | Fauver et al. | |
| 6,867,753 B2 | 3/2005 | Chinthammit et al. | |
| 6,904,308 B2 | 6/2005 | Frisch et al. | |
| 6,918,872 B2 | 7/2005 | Yokoi et al. | |
| 6,934,093 B2 | 8/2005 | Kislev et al. | |
| 6,934,573 B1 | 8/2005 | Glukhovsky et al. | |
| 6,936,003 B2 | 8/2005 | Iddan | |
| D510,139 S | 9/2005 | Gilad et al. | |
| 6,939,290 B2 | 9/2005 | Iddan | |
| 6,939,292 B2 | 9/2005 | Mizuno | |
| 6,944,316 B2 | 9/2005 | Glukhovsky et al. | |
| 6,950,690 B1 | 9/2005 | Meron et al. | |
| 6,958,034 B2 | 10/2005 | Iddan | |
| D512,150 S | 11/2005 | Iddan et al. | |
| 6,975,898 B2 | 12/2005 | Seibel | |
| 6,984,205 B2 | 1/2006 | Gazdzinski | |
| 6,986,738 B2 | 1/2006 | Glukhovsky et al. | |
| 7,009,634 B2 | 3/2006 | Iddan et al. | |
| 7,022,066 B2 | 4/2006 | Yokoi et al. | |
| 7,024,248 B2 | 4/2006 | Penner et al. | |
| 7,039,453 B2 | 5/2006 | Mullick et al. | |
| 7,060,094 B2 * | 6/2006 | Shahinpoor et al. | 623/4.1 |
| 7,109,859 B2 | 9/2006 | Peeters | |
| 7,118,529 B2 | 10/2006 | Glukhovsky et al. | |
| 7,118,531 B2 | 10/2006 | Krill | |
| 7,119,814 B2 | 10/2006 | Meron et al. | |
| 7,122,001 B2 | 10/2006 | Uchiyama et al. | |
| 7,140,766 B2 | 11/2006 | Glukhovsky et al. | |
| 7,160,258 B2 | 1/2007 | Imran et al. | |
| 7,161,164 B2 | 1/2007 | Glukhovsky | |
| 7,195,588 B2 | 3/2007 | Homan et al. | |
| 7,200,253 B2 | 4/2007 | Glukhovsky et al. | |
| D543,272 S | 5/2007 | Gilad et al. | |
| 7,251,383 B2 | 7/2007 | Iddan | |
| 7,295,226 B1 | 11/2007 | Meron et al. | |
| 7,307,544 B2 | 12/2007 | Kim et al. | |
| 7,316,647 B2 | 1/2008 | Kimoto et al. | |
| 7,319,896 B2 | 1/2008 | Konno | |
| 7,327,525 B2 | 2/2008 | Kislev et al. | |
| 7,336,833 B2 | 2/2008 | Horn | |
| 7,343,036 B2 | 3/2008 | Kleen et al. | |
| 7,347,817 B2 | 3/2008 | Glukhovsky et al. | |
| 7,348,571 B2 | 3/2008 | Ue | |
| 7,354,397 B2 | 4/2008 | Fujita et al. | |
| 7,452,338 B2 | 11/2008 | Taniguchi | |
| 7,488,287 B2 | 2/2009 | Kawashima | |
| 7,511,733 B2 | 3/2009 | Takizawa et al. | |
| 7,647,090 B1 | 1/2010 | Frisch et al. | |
| 7,664,174 B2 | 2/2010 | Avni et al. | |
| 7,775,977 B2 * | 8/2010 | Kawashima et al. | 600/437 |
| 7,805,178 B1 | 9/2010 | Gat | |
| 7,833,151 B2 | 11/2010 | Khait et al. | |
| 7,841,981 B2 | 11/2010 | Kawano et al. | |
| 7,866,322 B2 | 1/2011 | Iddan | |
| 7,872,667 B2 | 1/2011 | Iddan et al. | |
| 7,931,584 B2 | 4/2011 | Akagi et al. | |
| 7,940,603 B2 * | 5/2011 | Adachi et al. | 367/181 |
| 7,998,067 B2 | 8/2011 | Kimoto et al. | |
| 8,026,651 B2 * | 9/2011 | Wakabayashi et al. | 310/344 |
| 8,036,731 B2 | 10/2011 | Kimchy et al. | |
| 8,047,995 B2 * | 11/2011 | Wakabayashi et al. | 600/459 |
| 8,118,774 B2 * | 2/2012 | Dann et al. | 604/95.04 |
| 8,125,516 B2 | 2/2012 | Iddan et al. | |
| 8,647,259 B2 | 2/2014 | Arneson et al. | |
| 2001/0035902 A1 | 11/2001 | Iddan et al. | |
| 2002/0032366 A1 | 3/2002 | Iddan et al. | |
| 2002/0109774 A1 | 8/2002 | Meron et al. | |
| 2002/0138009 A1 | 9/2002 | Brockway et al. | |
| 2002/0158976 A1 | 10/2002 | Vni et al. | |
| 2002/0165592 A1 | 11/2002 | Glukhovsky et al. | |
| 2002/0168144 A1 | 11/2002 | Chen et al. | |
| 2002/0173718 A1 | 11/2002 | Frisch et al. | |
| 2002/0177779 A1 | 11/2002 | Adler et al. | |
| 2002/0193669 A1 | 12/2002 | Glukhovsky | |
| 2002/0198470 A1 | 12/2002 | Imran et al. | |
| 2003/0013370 A1 | 1/2003 | Glukhovsky | |
| 2003/0018280 A1 | 1/2003 | Lewkowicz et al. | |
| 2003/0020810 A1 * | 1/2003 | Takizawa et al. | 348/68 |
| 2003/0028078 A1 | 2/2003 | Glukhovsky et al. | |
| 2003/0040685 A1 | 2/2003 | Lewkowicz et al. | |
| 2003/0043263 A1 | 3/2003 | Glukhovsky et al. | |
| 2003/0045790 A1 | 3/2003 | Lewkowicz et al. | |
| 2003/0077223 A1 | 4/2003 | Glukhovsky et al. | |
| 2003/0114742 A1 | 6/2003 | Lewkowicz et al. | |
| 2003/0117491 A1 | 6/2003 | Avni et al. | |
| 2003/0139647 A1 | 7/2003 | Raz et al. | |
| 2003/0139661 A1 | 7/2003 | Kimchy et al. | |
| 2003/0174208 A1 | 9/2003 | Glukhovsky et al. | |
| 2003/0195415 A1 | 10/2003 | Iddan | |
| 2004/0019278 A1 * | 1/2004 | Abend | 600/454 |
| 2004/0027500 A1 | 2/2004 | Davidson et al. | |
| 2004/0032187 A1 | 2/2004 | Penner et al. | |
| 2004/0073087 A1 | 4/2004 | Glukhovsky et al. | |
| 2004/0109488 A1 | 6/2004 | Glukhovsky et al. | |
| 2004/0114856 A1 | 6/2004 | Kubby et al. | |
| 2004/0127785 A1 | 7/2004 | Davidson et al. | |
| 2004/0138532 A1 | 7/2004 | Glukhovsky | |
| 2004/0171915 A1 | 9/2004 | Glukhovsky et al. | |
| 2004/0176685 A1 * | 9/2004 | Takizawa et al. | 600/424 |
| 2004/0181155 A1 | 9/2004 | Glukhovsky | |
| 2004/0199054 A1 | 10/2004 | Wakefield | |
| 2004/0199061 A1 | 10/2004 | Glukhovsky | |
| 2004/0199222 A1 | 10/2004 | Sun et al. | |
| 2004/0202339 A1 | 10/2004 | O'Brien, Jr. et al. | |
| 2004/0204744 A1 | 10/2004 | Penner et al. | |
| 2004/0210105 A1 | 10/2004 | Hale et al. | |
| 2004/0220474 A1 * | 11/2004 | Abend et al. | 600/437 |
| 2004/0236182 A1 | 11/2004 | Iddan et al. | |
| 2004/0240077 A1 | 12/2004 | Kislev et al. | |
| 2004/0258328 A1 | 12/2004 | Adler | |
| 2004/0267127 A1 * | 12/2004 | Abend et al. | 600/450 |
| 2005/0004461 A1 * | 1/2005 | Abend | 600/437 |
| 2005/0025368 A1 | 2/2005 | Glukhovsky | |
| 2005/0065441 A1 | 3/2005 | Glukhovsky | |

(56) References Cited

U.S. PATENT DOCUMENTS

| | | |
|---|---|---|
| 2005/0068416 A1 | 3/2005 | Glukhovsky et al. |
| 2005/0075555 A1 | 4/2005 | Glukhovsky et al. |
| 2005/0088299 A1 | 4/2005 | Bandy et al. |
| 2005/0096526 A1* | 5/2005 | Reinschke .................... 600/407 |
| 2005/0110881 A1 | 5/2005 | Glukhovsky et al. |
| 2005/0119577 A1* | 6/2005 | Taniguchi .................... 600/459 |
| 2005/0143644 A1 | 6/2005 | Gilad et al. |
| 2005/0148816 A1 | 7/2005 | Glukhovsky et al. |
| 2005/0159643 A1 | 7/2005 | Zinaty et al. |
| 2005/0159789 A1 | 7/2005 | Brockway et al. |
| 2005/0171398 A1 | 8/2005 | Khait et al. |
| 2005/0177026 A1 | 8/2005 | Hoeg et al. |
| 2005/0185299 A1 | 8/2005 | Kislev et al. |
| 2005/0187433 A1 | 8/2005 | Horn et al. |
| 2005/0203417 A1* | 9/2005 | Okuno .......................... 600/463 |
| 2005/0222490 A1 | 10/2005 | Glukhovsky et al. |
| 2005/0228259 A1 | 10/2005 | Glukhovsky et al. |
| 2005/0228275 A1* | 10/2005 | Kawashima ................ 600/437 |
| 2005/0266074 A1 | 12/2005 | Zilberstein et al. |
| 2005/0272974 A1 | 12/2005 | Iddan |
| 2005/0279799 A1* | 12/2005 | Kubokawa et al. ........... 224/665 |
| 2005/0281446 A1 | 12/2005 | Glukhovsky et al. |
| 2006/0004256 A1 | 1/2006 | Gilad et al. |
| 2006/0009818 A1 | 1/2006 | Von Arx et al. |
| 2006/0036131 A1 | 2/2006 | Glukhovsky et al. |
| 2006/0045118 A1 | 3/2006 | Hyoung et al. |
| 2006/0074275 A1 | 4/2006 | Davidson et al. |
| 2006/0082648 A1 | 4/2006 | Iddan et al. |
| 2006/0092908 A1 | 5/2006 | Sung et al. |
| 2006/0116584 A1 | 6/2006 | Sudol et al. |
| 2006/0122461 A1 | 6/2006 | Kislev et al. |
| 2006/0132599 A1 | 6/2006 | Iddan et al. |
| 2006/0147037 A1 | 7/2006 | Boschetti |
| 2006/0149132 A1 | 7/2006 | Iddan |
| 2006/0155174 A1 | 7/2006 | Glukhovsky et al. |
| 2006/0158512 A1 | 7/2006 | Iddan et al. |
| 2006/0184039 A1 | 8/2006 | Avni et al. |
| 2006/0192889 A1 | 8/2006 | Iddan et al. |
| 2006/0232668 A1 | 10/2006 | Horn et al. |
| 2006/0238879 A1 | 10/2006 | Togino |
| 2006/0252371 A1 | 11/2006 | Yanagida |
| 2006/0252986 A1* | 11/2006 | Akagi et al. ................ 600/101 |
| 2007/0002135 A1 | 1/2007 | Glukhovsky |
| 2007/0002604 A1 | 1/2007 | Lin et al. |
| 2007/0043310 A1 | 2/2007 | Trandafir et al. |
| 2007/0060798 A1 | 3/2007 | Krupnik et al. |
| 2007/0060979 A1 | 3/2007 | Strother et al. |
| 2007/0078335 A1 | 4/2007 | Horn |
| 2007/0123772 A1 | 5/2007 | Euliano et al. |
| 2007/0185381 A1* | 8/2007 | Kimoto et al. ................ 600/117 |
| 2007/0213659 A1 | 9/2007 | Trovato et al. |
| 2007/0221233 A1* | 9/2007 | Kawano et al. ............. 128/899 |
| 2007/0232874 A1 | 10/2007 | Ince |
| 2007/0264732 A1* | 11/2007 | Chen .............................. 438/22 |
| 2007/0265496 A1* | 11/2007 | Kawano et al. .............. 600/109 |
| 2007/0282156 A1 | 12/2007 | Konings |
| 2008/0015411 A1 | 1/2008 | Kimoto et al. |
| 2008/0058597 A1 | 3/2008 | Arneson et al. |
| 2008/0146871 A1 | 6/2008 | Arneson et al. |
| 2008/0213355 A1 | 9/2008 | Bohmer |
| 2009/0088618 A1 | 4/2009 | Arneson et al. |
| 2009/0253999 A1* | 10/2009 | Aoki et al. .................... 600/565 |
| 2010/0130822 A1* | 5/2010 | Katayama et al. ........... 600/118 |
| 2010/0179381 A1* | 7/2010 | Kawano et al. ............. 600/104 |
| 2010/0217079 A1* | 8/2010 | Tichy ............................ 600/118 |
| 2010/0251823 A1* | 10/2010 | Adachi et al. ................. 73/606 |
| 2010/0268058 A1* | 10/2010 | Chen ............................ 600/407 |
| 2011/0060189 A1* | 3/2011 | Belson .......................... 600/117 |

FOREIGN PATENT DOCUMENTS

| | | |
|---|---|---|
| EP | 1637917 A1 | 3/2006 |
| EP | 1654983 A1 | 5/2006 |
| EP | 1676522 A1 | 7/2006 |
| EP | 1693000 A2 | 8/2006 |
| EP | 1698278 A1 | 9/2006 |
| EP | 1704812 A1 | 9/2006 |
| EP | 1707105 A1 | 10/2006 |
| EP | 1715697 A2 | 10/2006 |
| EP | 1737124 A2 | 12/2006 |
| GB | 2414408 A | 11/2005 |
| WO | WO 02/054932 A2 | 7/2002 |
| WO | WO 02/055126 A2 | 7/2002 |
| WO | WO 02/055984 A2 | 7/2002 |
| WO | WO 02/073507 A2 | 9/2002 |
| WO | WO 02/080376 A2 | 10/2002 |
| WO | WO 02/080753 A2 | 10/2002 |
| WO | WO 02/089913 A2 | 11/2002 |
| WO | WO 02/094337 A2 | 11/2002 |
| WO | WO 03/003706 A2 | 1/2003 |
| WO | WO 03/010967 A1 | 2/2003 |
| WO | WO 03/028224 A2 | 4/2003 |
| WO | WO 03/053241 A2 | 7/2003 |
| WO | WO 2004/014227 A1 | 2/2004 |
| WO | WO 2004/052209 A1 | 6/2004 |
| WO | WO 2004/054430 A2 | 7/2004 |
| WO | WO 2004/058041 A2 | 7/2004 |
| WO | WO 2004/096008 A2 | 11/2004 |
| WO | WO 2005/062715 A2 | 7/2005 |
| WO | WO 2006/005075 A2 | 1/2006 |
| WO | WO 2006/034125 A2 | 3/2006 |
| WO | WO 2006/059331 A2 | 6/2006 |
| WO | WO 2006/070367 A2 | 7/2006 |
| WO | WO 2006/103665 A2 | 10/2006 |
| WO | WO 2006/114649 A1 | 11/2006 |
| WO | WO 2007/028035 A2 | 3/2007 |
| WO | WO 2007/126246 A2 | 11/2007 |
| WO | WO 2007/126247 A1 | 11/2007 |
| WO | WO 2007/143200 A2 | 12/2007 |
| WO | WO 2007/149559 A2 | 12/2007 |
| WO | WO 2008/014432 A2 | 1/2008 |
| WO | WO 2008/016194 A2 | 2/2008 |
| WO | WO 2009/022343 A2 | 2/2009 |

* cited by examiner

Graph of acoustic power at focal point at constant radius, and Y=0

$FWHM_\theta = 0.646$ deg $FWHM_x = 0.118$ mm $\dfrac{FWHM_x}{\lambda} = 0.879$

Graph of acoustic power at focal point at constant radius, and θ=0

$FWHM_y = 0.305$ mm $\dfrac{FWHM_y}{\lambda} = 2.261$

ULTRASOUND SCANNING CAPSULE ENDOSCOPE

CROSS-REFERENCE TO RELATED APPLICATIONS

The present application is a continuation of U.S. patent application Ser. No. 13/073,424, filed Mar. 28, 2011, now U.S. Pat. No. 8,647,259, which claims the benefit under 35 U.S.C. §119(e) to U.S. Provisional Patent Application No. 61/318,012, filed on Mar. 26, 2010, entitled "Ultrasound Scanning Capsule Endoscope (USCE)," each of which are incorporated by reference herein in their entireties.

FIELD OF THE INVENTION

The present invention relates to ultrasound imaging on a capsule endoscope platform. It relates to the generation of a focused ultrasound acoustic signal and the receiving of echo signals from the wall of a body lumen with an array of acoustic transducers wrapped around the circumference of the capsule. It relates to sending the generated echo image signals to receiver devices attached or worn on the body. It relates to the generation of 360° overlapping sidewall ultrasound scans of a body lumen, and image processing techniques to assemble these scans into a high resolution continuous ultrasound image. Finally, it relates to the manufacture and assembly of such an ultrasound scanning capsule endoscope (USCE). The concept is extendable to conventional endoscopes and catheters.

BACKGROUND OF THE INVENTION

The population of the United States is aging. The first wave of the 78 million "Baby Boomers" is beginning to turn 60 years old. Coinciding with this aging of population is a rising concern regarding the public health, and a generally more educated patient in technology awareness. Some conditions, such as cancer, are most responsive to treatment if caught in the early stages. Cancer, for example, is best detected in the digestive tract. Given that cancerous growth can occur in as little as one to two years, it is essential to detect cancer or cancerous precursors at least annually, or preferably biannually. Physician and health care resources are currently already stretched and will fail if the current technology, process and procedure are not altered to suit the needs of the baby boomer market of the near future. Time-saving and simple solutions to diagnostics are needed.

The current population desires speedy testing and fast answers to their health questions. Many current testing and monitoring systems are limited by old technology and processes that takes days if not weeks for results. These test methods if not inconvenient and potentially embarrassing are at least in most cases intrinsically painful or risky to patients.

Thus, what is needed are diagnostic devices, services and processes that are simple, convenient, relatively inexpensive, comfortable, take less time, directly detect specific compounds or indicators to disease, and have more applications.

BRIEF DESCRIPTION OF THE DRAWINGS/FIGURES

The accompanying drawings illustrate the present invention and, together with the description, further serve to explain the principles of the invention and to enable one skilled in the pertinent art to make and use the invention.

DETAILED DESCRIPTION OF THE INVENTION

Introduction

Novel approaches to small bowel capsule endoscopy that uses an optical train to capture 360° overlapping sidewall scans of the small bowel, and image processing techniques to assemble these scans into a high resolution continuous image have been developed. This Optical Scanning Capsule Endoscope (OSCE) is a revolutionary step forward providing for 100% coverage of the intestinal tract including the small and large bowels. The image assembly techniques are not specific to optical images, which provide the opportunity to replace the optical imaging hardware with ultrasound imaging. An Ultrasound Scanning Capsule Endoscope (USCE) is envisioned which would use ultrasound imaging elements in an annular (ring-like) array around the circumference of the capsule to produce an image of reflected acoustic energy from the body lumen wall, and would use the same signal processing algorithms to assemble sequential ring scan frames into a single continuous image of the colon. Because the ultrasound signal would be reflected from the interface between the colonic contents and the colon tissue itself, it may not be necessary to prep the patient for this procedure. This sidewall ring scanning approach, when extended to ultrasound imaging rather than optical imaging, could enable prep-less imaging of the colon for Colorectal Cancer screening.

The OSCE technology platform effectively implements a 256 to 512 by 16 to 32 element wide optical scanning array around the circumference of a nominally 11 millimeter diameter capsule. It operates at up to 60 frames per second to accommodate rapid peristalsis movement (up to 5 cm per second) and tumbling. Optical flow algorithms, similar to those used in optical mice for computers, are used to track capsule movement. This movement information is used to vary the scan rate to minimize scan redundancy when stationary. Stitching algorithms, similar to those commercially available, are used to construct a single image of the entire intestine, which can be viewed and manipulated much like Google maps. The scan data is transmitted from the capsule to on-body sensors using the acoustic data communication technology described herein.

The USCE will be implemented by replacing the optical scanning array with an ultrasound scanning array. This scanning array swap will be built on top of the technology platform developed for the OSCE. The proposed USCE technical approach is described in detail below.

Figure 1:
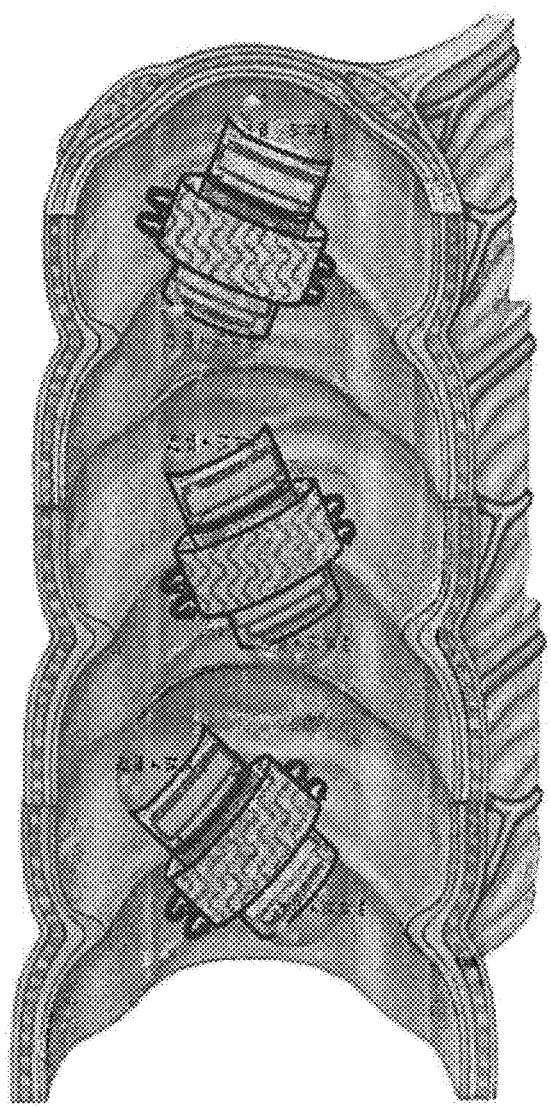
FIG. 1 is a drawing of the USCE in the intestinal tract.
Figure 2:
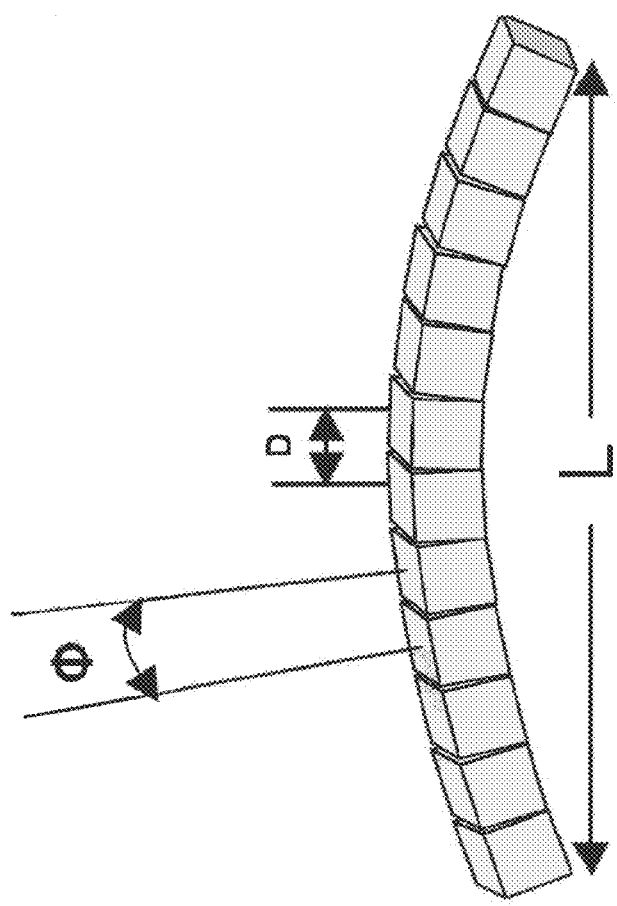
FIG. 2 is a drawing of the acoustic transducer array encircling the capsule endoscope.
Figure 3:
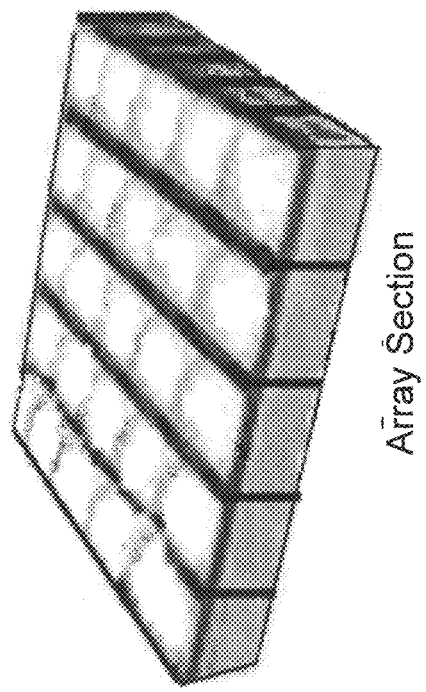
FIG. 3 shows the construction of a section of the transducer array.

Key Design Considerations:

There are several key design trade-offs that need to be considered to optimize the performance of the ultrasound scanner involving frequency of operation, acoustic element size and surface area, array size, transmit and receive power, battery current, and desired "image" voxel size, which is the spot size of the focused acoustic energy on the intestinal wall. FIG. 1 is an illustration of the USCE in the intestinal tract, showing how the focused acoustic energy impinges on the intestinal wall and is reflected back to the capsule. FIG. 2 illustrates the transducer array wrapped around the circumference of the capsule. The acoustic transducers could be implemented with PZT elements, but other technologies could also be employed. FIG. 3 shows a section of the array, illustrating its cross section. For the following discussion, the term "phased array" signifies the part of the total array that is energized for the generation of a focused acoustic signal at a spot on the intestinal wall.

The smallest spot size, $S_p$, defined as the diameter of the focused energy between first zeros, that acoustic energy may be focused to is given by:

$$S_p = 2\lambda l_f / L, \quad (1)$$

where L is the side dimension of the phased array, and lf is the focal length, given by the distance, d, from the array center to the intestinal wall. The wavelength of the sinusoidal acoustic signal is $\lambda = c/f$ where c=1540 meters/sec is the speed of sound in the aqueous environment of the intestinal track, and f is the signal frequency.

The depth of focus, $F_d$ is then given by:

$$F_d = S_p^2 / (2\lambda). \quad (2)$$

For a given focal length, the spot size is determined by $\lambda$ and L, both of which have practical limits. The wavelength is limited by signal attenuation and L is limited by the curvature of the capsule. The term $l_f / L$ is the f-number which in practice is hard to get much smaller than unity, which limits the spot size to somewhat less than $2\lambda$, to no smaller than $\lambda$. The depth of focus increases as spot size increases, and some cases it may be desirable to increase the depth of focus at the expense of increased spot size, such as for when d is not well known. The optimization of $\lambda$ and L for array performance are next considered.

Figure 4:
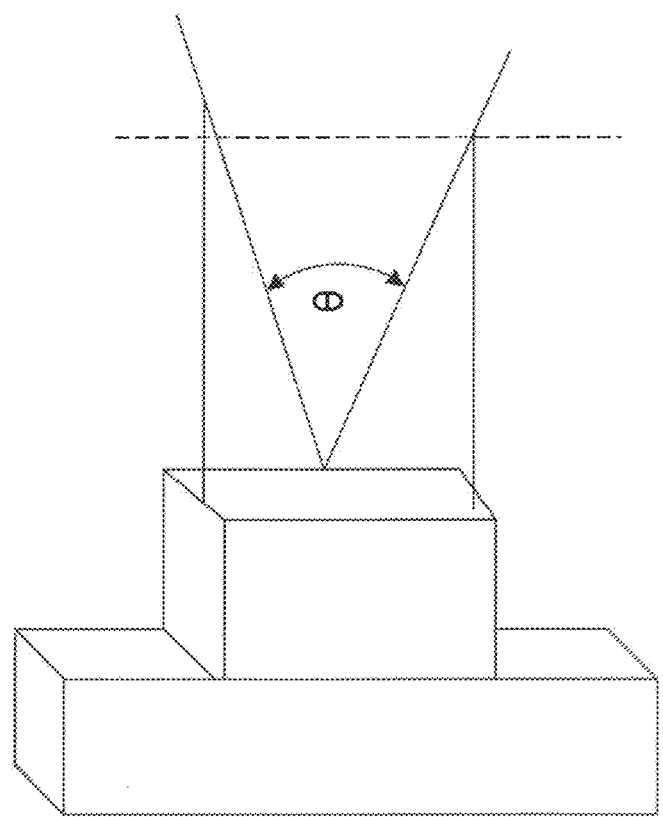
FIG. 4 illustrates the acoustic signal divergence angle from a single acoustic transducer element.

For optimal operation, the operational frequency needs to be chosen so that its wavelength, $\lambda$, is a multiple of the center-to-center transducer element spacing, D. Hence, $\lambda = mD$, where m=1 or 2 for this example implementation, although other values could be used and still fall under the scope of this invention. For a given D, m=1 would appear to provide for the smallest spot size from equation (1). But the focused array dimension, L, is constrained by the signal divergence angle, $\Theta$, from the acoustic transducer elements, as shown in FIG. 4 and given by:

$$\Theta = \sin^{-1}(K\lambda/D), \quad (3)$$

where K=0.433 for the half power point of the signal.

Figure 5:
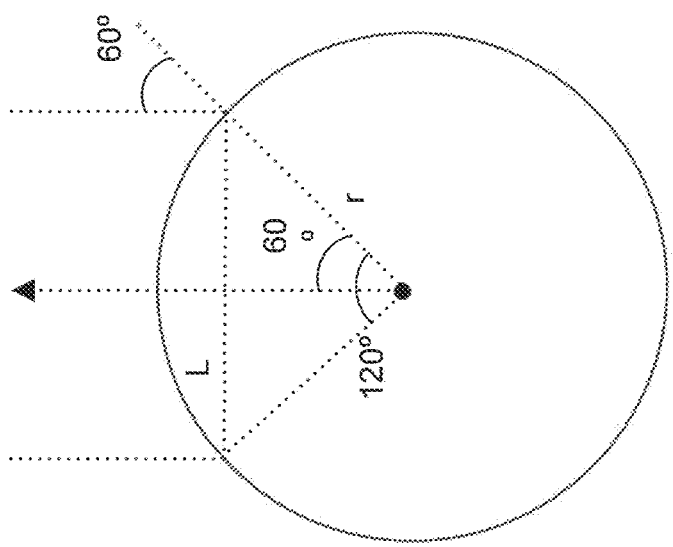
FIG. 5 shows the maximum phased array size around the capsule circumference.

For $\lambda = 2D$, the acoustic signal half power point occurs at $\Theta = 60°$. For $\lambda = D$, $\Theta = 26°$. The resulting difference in array size between these two angles is significant because of the surface curvature around the circumference of the capsule. Because of this curvature, the circumference transducer elements will have an angle between the elements, as shown on FIG. 2, given by:

$$\Phi = 360°/N \quad (4)$$

where N is the number of acoustic transducer elements around the circumference. The maximum array size for the circumference transducer elements is limited by the resultant curvature angle of the edge elements relative to the image spot. For $\lambda = 2D$, this will be the $\Theta = 60°$ divergence angle. The maximum focused array size is achieved in the limit of a very large imaging distance (going theoretically to infinity) between the intestinal wall and the center of the acoustic transducer element array where the array around the circumference would be a full third of the circumference (120°). However, the effective array aperture is the planar projection of this arc as shown in FIG. 5:

$$L_{max} = 2r \sin(\Theta) = 2rK\lambda/D, \quad (5)$$

from equation (3) above, and where r is the radius of curvature of the capsule. For $\Theta = 60°$ provided by $\lambda = 2D$, $L_{max2} = 4rK$. For $\Theta = 26°$ provided by $\lambda = D$, $L_{max1} = 2rK$, which is half the value of $L_{max2}$. Therefore, either case for $\lambda$ provides for the same spot size from equation (1) in the theoretical limit of infinite image distance. Using $L_{max}$ in equation (1) shows that for L near $L_{max}$ the spot size in the circumference direction increases linearly with d=lf:

$$S_{plimit} = \frac{Dl_f}{rK}. \quad (6)$$

The array size in the axial direction is also constrained by the divergence angle through the relation:

$$L_{axial} = 2l_f \tan(\Theta). \quad (7)$$

For $\Theta = 60°$, provided by $\lambda = 2D$, $L_{axial} = 3.5 \, l_f$, for which the f-number=$l_f / L_{axial} = 0.29$. The spot size in the axial direction is then:

$$S_{paxial} = \frac{4D}{3.5} = 1.15D. \quad (8)$$

Because the f-number is much less than one, this spot size is probably not practically achievable. For $\Theta=26°$, provided by $\lambda=D$, $L_{axial}=l_f$ for which the f-number=1 and the spot size in the axial direction is:

$$S_{paxial}=2D. \quad (9)$$

Figure 6:
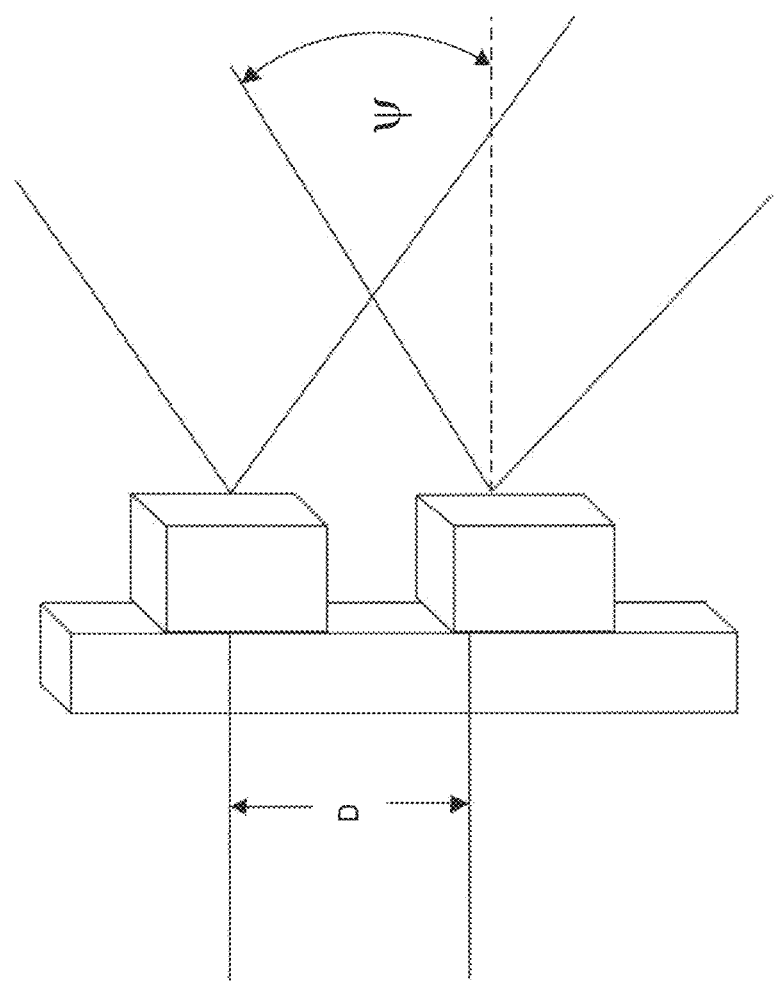
FIG. 6 illustrates the concept behind the array grating lobes.

Another key design consideration is the resulting signal pattern projected by the array. Of particular interest is what is termed the "grating" pattern, determined by:

$$\Psi_{gn}=\sin^{-1}(n\lambda/D) \quad (10)$$

where the center to center spacing of the transducer elements, D, is shown in FIG. 6 and $$n = n = \pm 1, 2, 3,$$

etc. for the grating lobes. The locations of the grating lobes are for the following parameters:

$$\lambda = 2D, \Psi_{gn} = \text{N/A (no grating lobe)} \quad (a)$$

$$\lambda = D, \Psi_{gn} = \pm 63° \quad (b)$$

For choice (a) above only the center beam is present with no grating lobes to confuse or complicate receiving an unambiguous ultrasound echo signal. Hence, the optimal design choice for the acoustic transducer array is $\lambda=2D$.

An example implementation is to implement N=512 transducer elements around a capsule diameter of 11 mm requiring a center-to-center spacing of D=67.5 microns for adjacent elements. A 10% overhead for spacing between elements gives a net transducer element size of 60 microns on a side, with 3.25 microns between elements. The wavelength is $\lambda=2$ D=135 microns, which provides for a frequency of 11.4 MHz and a divergence angle of $\Theta=60°$. Other design selections would fall under the scope of this invention. The maximum theoretical focused array size is considered to be one third of the circumference ($2\Theta=120°$) for an arc length of 11.5 mm, which accommodates 170 elements. The planar projection is $L_{max}=9.5$ mm. The array dimension in the axial direction is given by $L_{axial}=3.5\ l_f$. However, a practical focused array size may be smaller than this because of the tradeoff between spot size and operational complexity. Smaller arrays are simpler to implement, but the resulting spot size will be larger. Here, the practical array size will be limited to 32 transducer elements in the axial direction.

Scanner Operation:

The phased array is set in the transmit configuration to launch a brief pulse focused to the minimum spot size at the targeted $l_f$ value, which could be the previously measured value for that voxel. The signal is focused by driving each element in the array with the appropriate timing so that the resulting wave front converges at the targeted spot. This is done with conventional approaches used in medical ultrasound imaging systems, except that the curvature of the array around the circumference needs to be accommodated in the signal timing to each element. Since the spot is not scanned, but is fixed to coincide with a point above the center of the array, the timing circuits are simplified by the array quadrant symmetry. So the number of timing circuits will be ¼ of the total number of transducer elements in the array. The timing circuits are further simplified by using one counter for the timer, with taps off the counter at the appropriate points for the correct timing of each transducer element in symmetric positions in all four quadrants. So four transducer elements are driven from each counter tap. The circuitry is further simplified by eliminating the 11.4 MHz oscillator circuit to drive the transducer elements for a short pulse, but by rather inducing resonant oscillation at 11.4 MHz with a brief impulse to the transducer elements. However, using an oscillator to drive the transducer elements would fall under the scope of the invention. The counter taps are programmable with algorithms that take the previous measurement data to set the appropriate timing taps for the next measurement.

Once the pulse has been launched, the array is configured into the receive mode, to listen for the signal echoes. In conventional medical ultrasound, the same phase array timing is used in the receive mode as for the pulse transmit mode. This approach is very complex, and requires a separate "front end" at each transducer element to detect a very weak return signal. However, because the transmit array provides a very well defined spot signal with no grating lobes, the receive array can be greatly simplified to just a small array of transducer elements at the center of the larger transmit array.

Medical ultrasound imaging receives multiple echo signals to re-construct a depth image of the object. Here, the USCE will be limited by the bandwidth of the communication channel to how much data can be acquired and sent.

The scanning operation is achieved by pulsing a single or multiple phased arrays configured around the circumference of the capsule. Once the echo signal is captured, a switching array configures the array elements for the next phased array, one element over around the circumference from the previous. In this way, one or multiple voxels around the array circumference are imaged at a time in sequence until all the circumference voxels have been imaged and the surface around the pill has been mapped. Then the process repeats using previously obtained data to set the arrays for the next data acquisitions. This process occurs very rapidly, resulting in a high net scan, or frame rate, whereby the capsule moves only a fraction of a voxel during peristalsis or tumbling, allowing for image stitching to capture a continuous, scanned image, as the capsule moves through the intestinal tract.

This scanning process measures a limited range of echo return times around expected echo times at the beam focus. The reflecting surface distance from the array is extracted from the dominant echo return time. This extracted surface distance is used as the focal distance for the next shifted voxel "probe". In this way the acoustic focus will closely follow the intestinal surface. An initial voxel scan will be need to gain the surface "lock", after which the scanning will be rapid.

Figure 7:
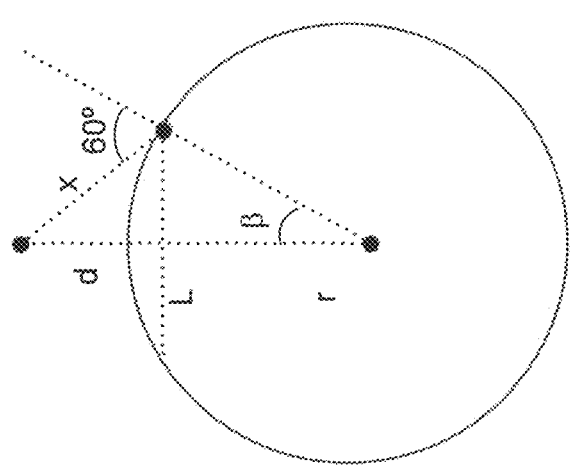
FIG. 7 shows the effective array aperture for the curved array for a particular focal distance.

An example of the above is provided for a distance of d=5 mm of the intestinal wall from the center of the transducer array. As discussed above, the array size, L, is limited by the curvature of the capsule, as shown in FIG. 7. The array size is given by:

$$L = 2r\sin(\beta), \text{ where from the law of cosines} \quad (11)$$

$$\beta = \tan^{-1}\left(\frac{.866}{.5 + \frac{r}{x}}\right), \text{ and} \quad (12)$$

Figure 8A:
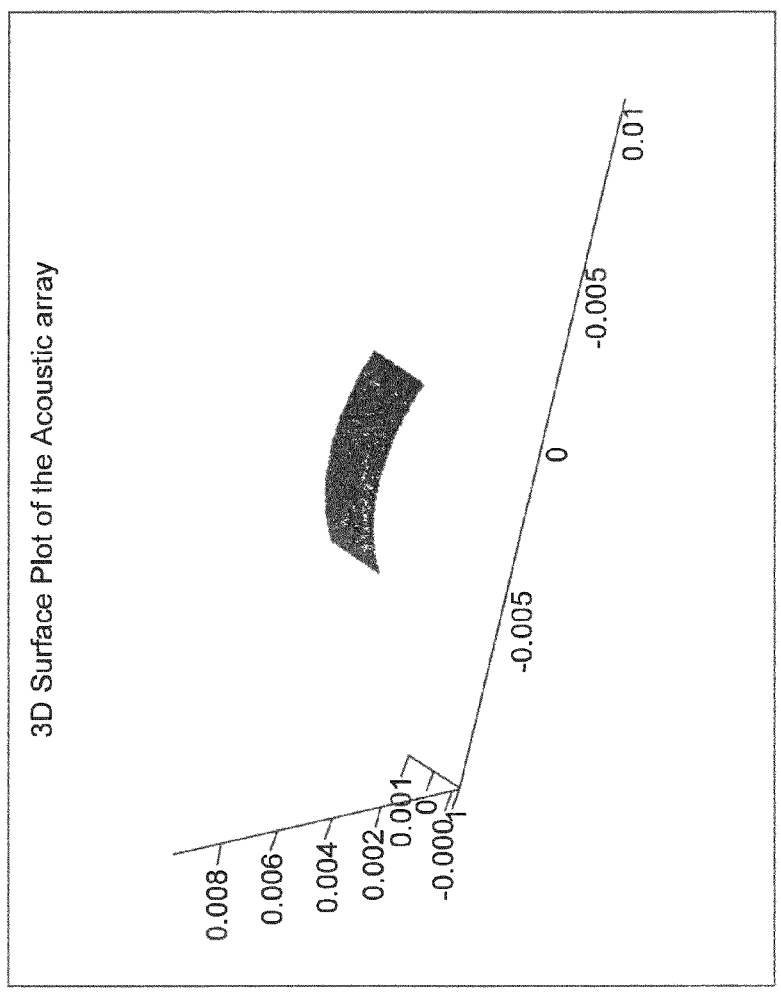
FIG. 8a shows a phased array configured to provide a focused acoustic beam for a simulation of the focused acoustic beam at a focal distance 5 mm away from the array surface.
Figure 8B:
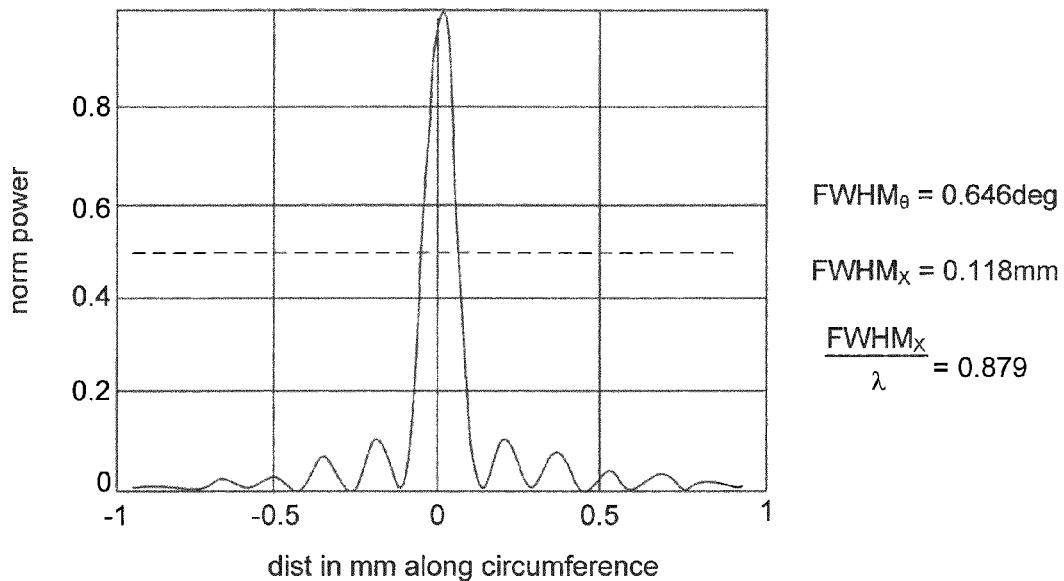
FIG. 8b is a graph of the resulting acoustic power at the focal point in the direction of the circumference and along the axial direction.
Figure 8B:
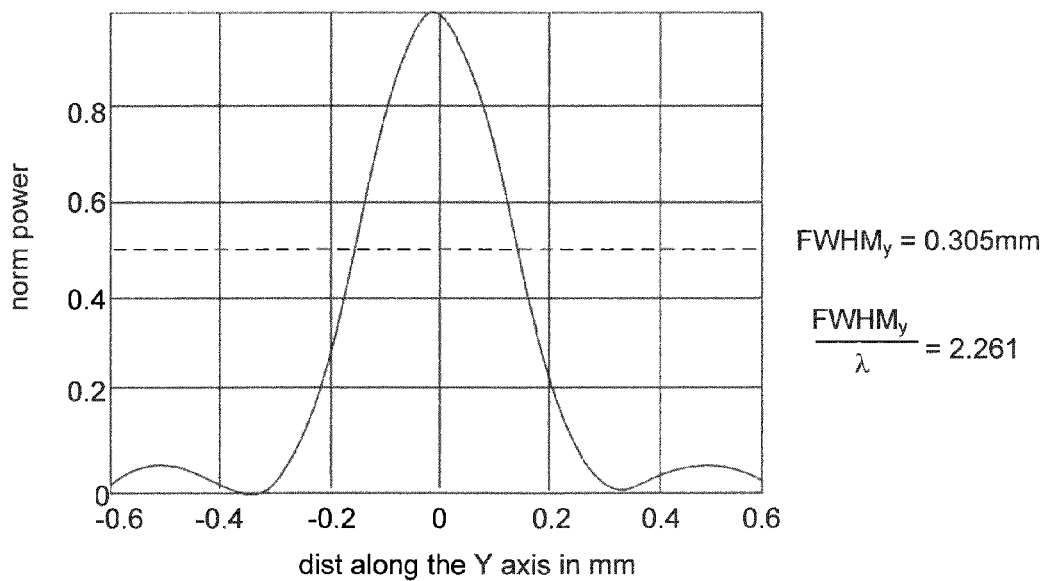
Figure 8C:
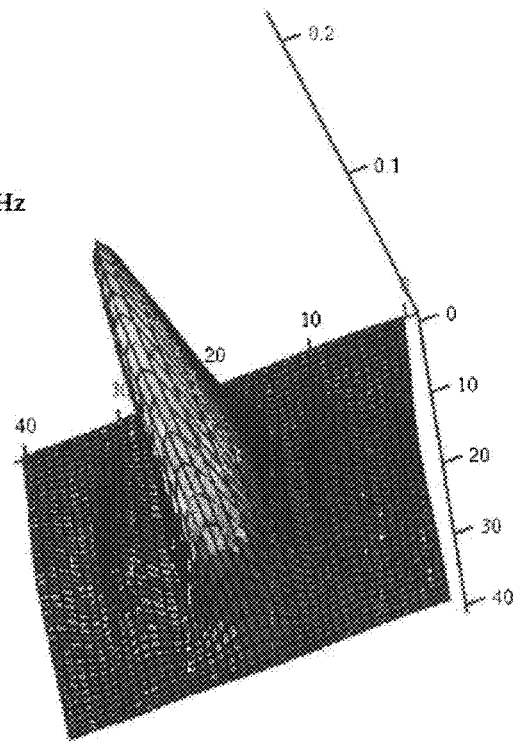
FIG. 8c is a three-dimensional presentation of the acoustic power, along with a top-down view.
Figure 8C:
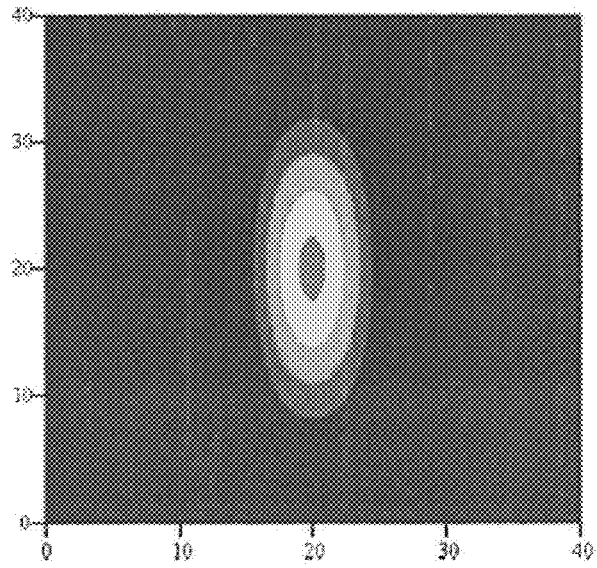

-continued $$x = -\frac{r}{2}\left[1 - \sqrt{1 + \frac{4d^2}{r^2}\left(1 + \frac{2r}{d}\right)}\right],\quad (13)$$

where r is the capsule radius. For d=5 mm, L=6 mm, and the selected phased array has 94 circumference transducer elements on a side. Using this value of L in equation (1) provides a theoretical spot size of 225 microns in the circumference direction, which provides the projected voxel size on the intestinal wall. The Mathcad simulation of FIGS. 8a-8c gives a circumference spot size of 242 microns between first zeroes. In the axial direction the number of transducer elements is 32, for an array dimension of 2 mm, which provides for a spot size of 625 microns. The Mathcad simulation gives an axial spot size of 654 microns between first zeroes. Therefore, the simulations confirm the theoretical predictions.

The number of such arrays, p, that can be "fired" at a time spaced equally around the capsule is in this case p=4. So four acoustic image voxels can be acquired in one transmit pulse period. Assuming a two wavelength acoustic pulse provides a total pulse period time of 0.175 usec. The maximum acoustic travel distance is from the array corners to the focused spot, given by:

$$d_{corner} = \sqrt{x^2 + \left(\frac{L_{axial}}{2}\right)^2},\quad (14)$$

which for this example is 0.67 cm, providing for a round trip distance of 1.34 cm, which takes 8.7 usec. The total voxel acquisition time is therefore $t_a$=8.87 usec, which establishes the maximum voxel acquisition rate of:

$$R_{pixel} = \frac{p}{t_a},\quad (15)$$

which for this case is 0.45 M voxels/sec. A complete scan of all the circumference voxels takes:

$$t_{scan} = \frac{Nt_a}{p} = \frac{N}{R_{pixel}},\quad (16)$$

which for this case is 1.135 msec, providing for a scan rate of 881 scans/sec where each scan is comprised of 512 circumference voxels. During one scan the capsule moves 0.09 of a spot size in the axial direction at the maximum peristalsis rate of 2 inches/sec. The resulting voxel overlap between scans allows for image stitching to provide a continuous scanned image. Note that the above translates the array one transducer element center-to-center distance, or 67.5 microns, around the circumference for the next transmit pulse and echo receive cycle, which is 0.25 of the spot size for the circumference array. If the array is translated two transducer elements between cycles, or a 0.5 of a circumference spot size, then the scan rate doubles with the same data output rate, and the capsule then moves 0.045 of a spot size in the axial direction between scans, for greater voxel overlap, which enables post image processing that could increase effective resolution by at least a factor of two. Conversely, the scan rate can be kept the same to halve the data rate, which could be an important data bandwidth consideration.

The data channel will limit how many return echoes can be acquired and sent. If just one return echo were acquired, which would provide a topographical image of the intestinal wall, along with the echo signal strength, two digitized data values would have to be sent for each voxel. Assuming 8 bits per data value would yield a total of 16 bits/voxel times 0.45 Mvoxels/sec=7.2 Mbits/sec, which could be achieved by a variety of approaches and still fall under the scope of the invention. If data compression could be used, then for 10× data compression the channel would only have to provide for 0.72 Mbits/sec.

Prep-less colon applications will most likely require more echo data to resolve the signal traveling through non-homogeneous intestinal material. For this application, a higher data rate communication channel will need to be employed. Each echo time and signal strength data pair will require 7.2 Mbits/sec of bandwidth. Ten pairs would require 72 Mbits/sec, which with 10× data compression would require a 7.2 Mbit/sec channel. The actual number of data pairs required will most likely be less than ten, lessening the data rate requirements.

Figure 9A:
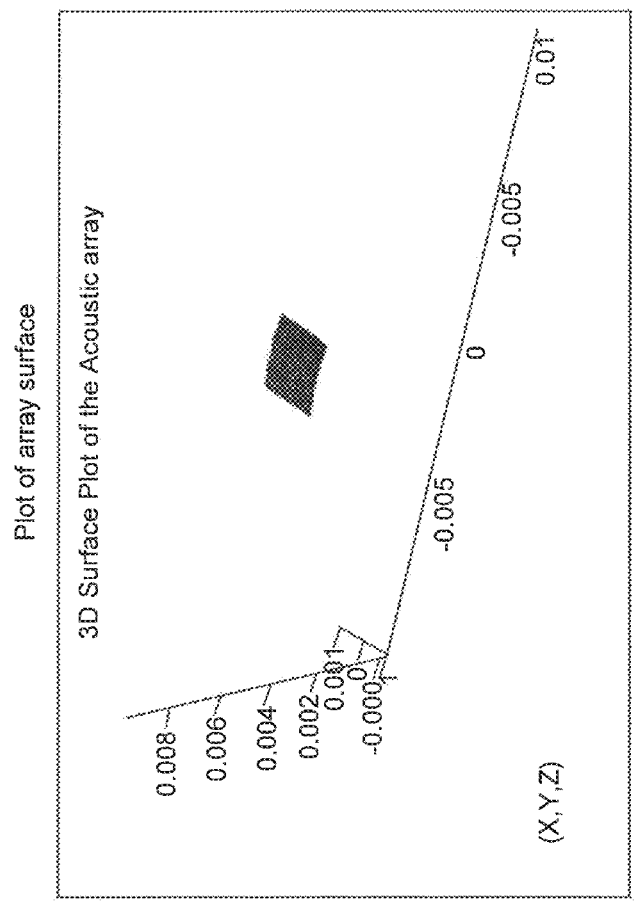
FIG. 9a shows a phased array configured to provide a focused acoustic beam for a simulation of the focused acoustic beam at a focal distance 1 mm away from the array surface.
Figure 9B:
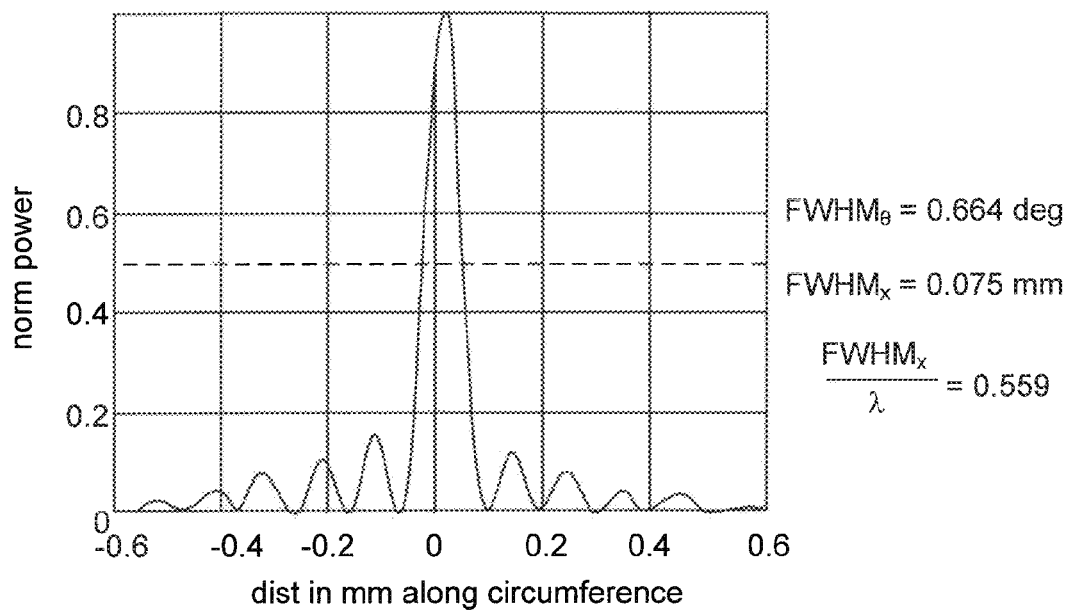
FIG. 9b is a graph of the resulting acoustic power at the focal point in the direction of the circumference and along the axial direction.
Figure 9B:
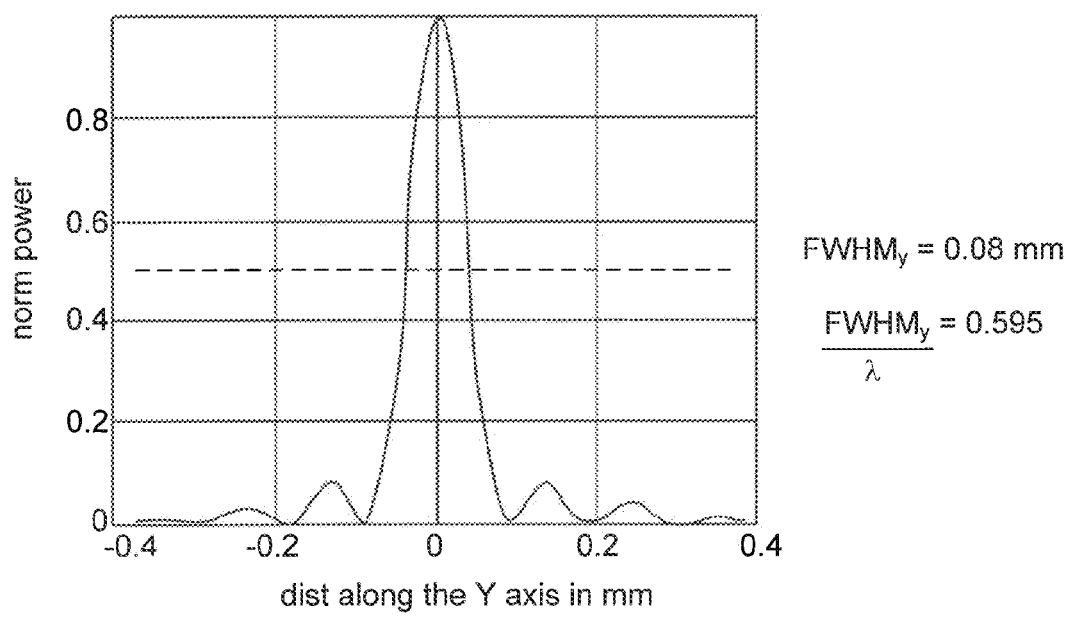
Figure 9C:
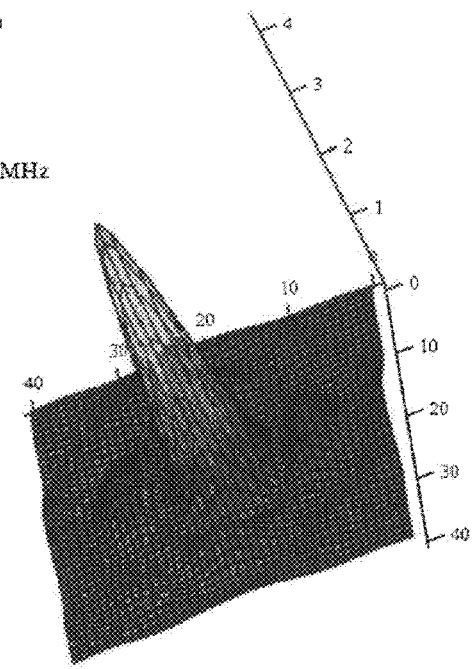
FIG. 9c is a three-dimensional presentation of the acoustic power, along with a top-down view.
Figure 9C:
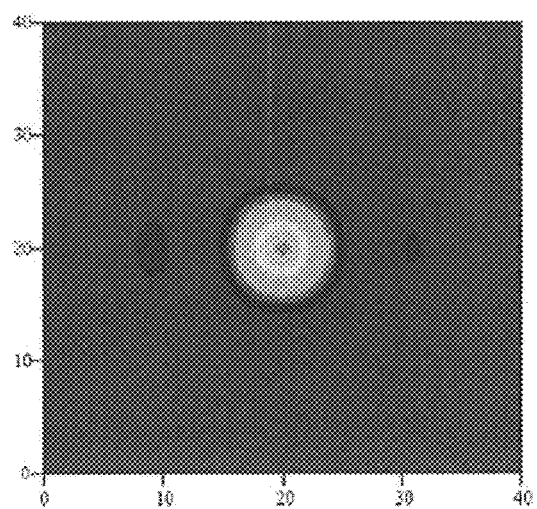

It is instructive to look also at calculations for when the intestinal wall is closer to the capsule. For a distance of d=$l_f$=1 mm of the intestinal wall from the transducer array, the array size is given by equation (11) to be L=2.45 mm comprising 36 transducer elements on a side. Using these values of L and $l_f$ in equation (1) provides an f-number of 0.4 and a theoretical spot size of 110 microns in the circumference direction. Because the f-number is much less than one, this spot size may not be realistically achievable. Indeed, the Mathcad simulation of FIGS. 9a-9c yields a spot size of 145 microns between first zeroes. In the axial direction the number of transducer elements is 32, for an array dimension of 2 mm, which provides for a spot size of 125 microns and an f-number of 0.46. Again, because the f-number is much less than one, this spot size may not be realistically achievable. Indeed, the Mathcad simulation of FIG. 9 yields a spot size of 170 microns.

Eight such arrays can be "fired" at a time equally spaced around the circumference of the capsule, for p=8. So eight acoustic image voxels can be acquired in one transmit pulse period. Repeating the calculations above for this yields $t_a$=2.76 usec, which establishes the maximum voxel acquisition rate of $R_{voxel}$=2.9 M voxels/sec and $t_{scan}$=0.177 msec, providing for a scan rate of 5660 scans/sec where each scan is comprised of 512 circumference voxels. During one scan the capsule moves 0.08 of a spot size width in the axial direction at the maximum peristalsis rate of 2 inches/sec. This overlap between scans allows for image stitching to provide a continuous scanned image. As with the previous discussion, the array can be stepped by two transducer elements around the circumference to either increase the axial voxel overlap by a factor of two, or to reduce the scan rate, and, therefore, reduce the required data rate.

Figure 10A:
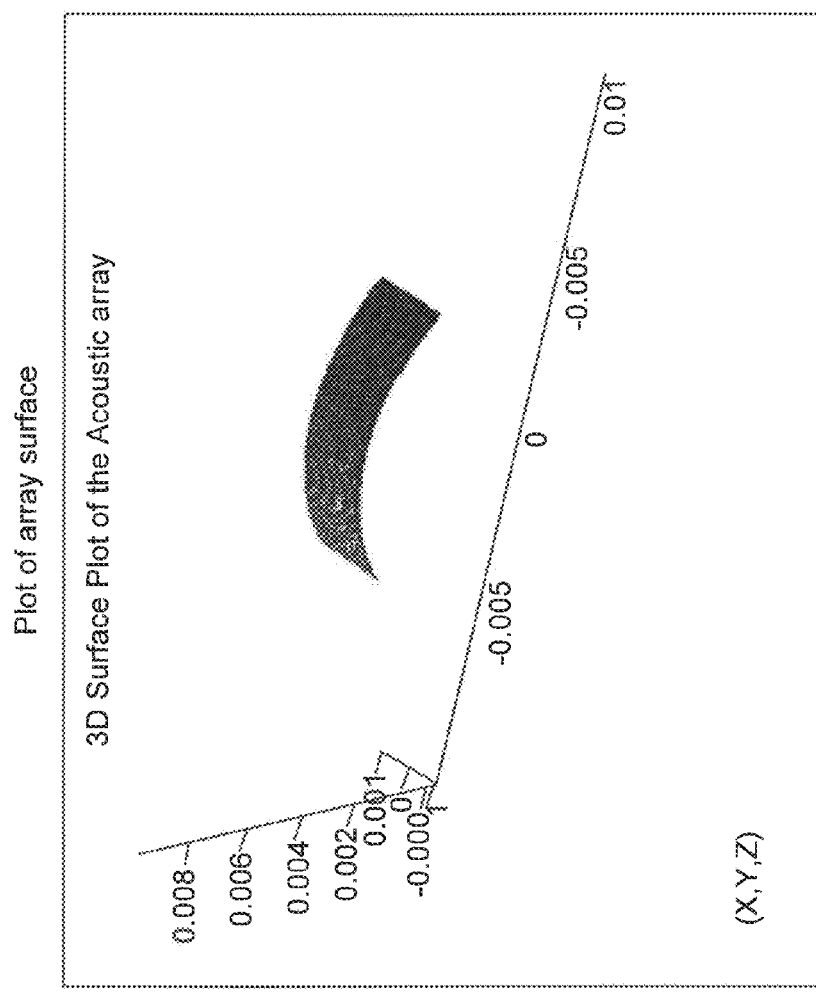
FIG. 10a shows a phased array configured to provide a focused acoustic beam for a simulation of the focused acoustic beam at a focal distance 10 mm away from the array surface.
Figure 10B:
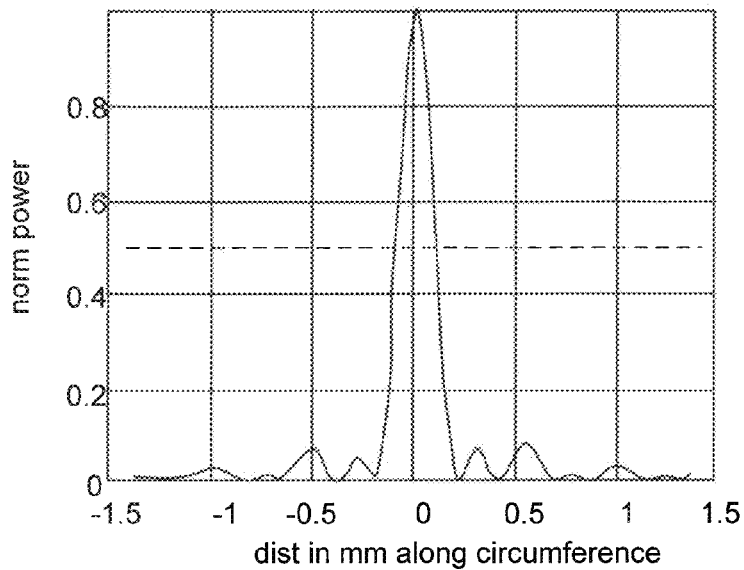
FIG. 10b is a graph of the resulting acoustic power at the focal point in the direction of the circumference and along the axial direction.
Figure 10B:
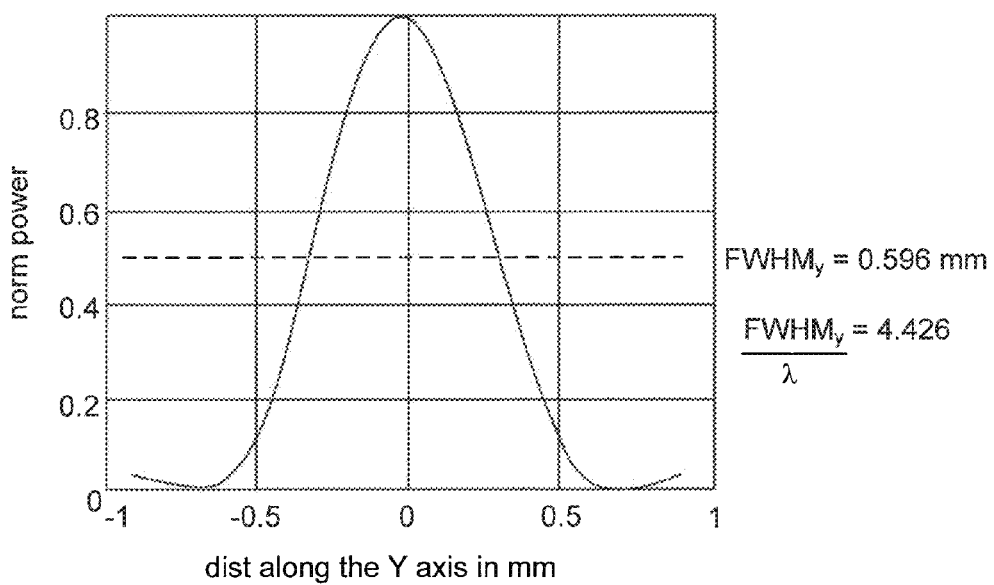
Figure 10C:
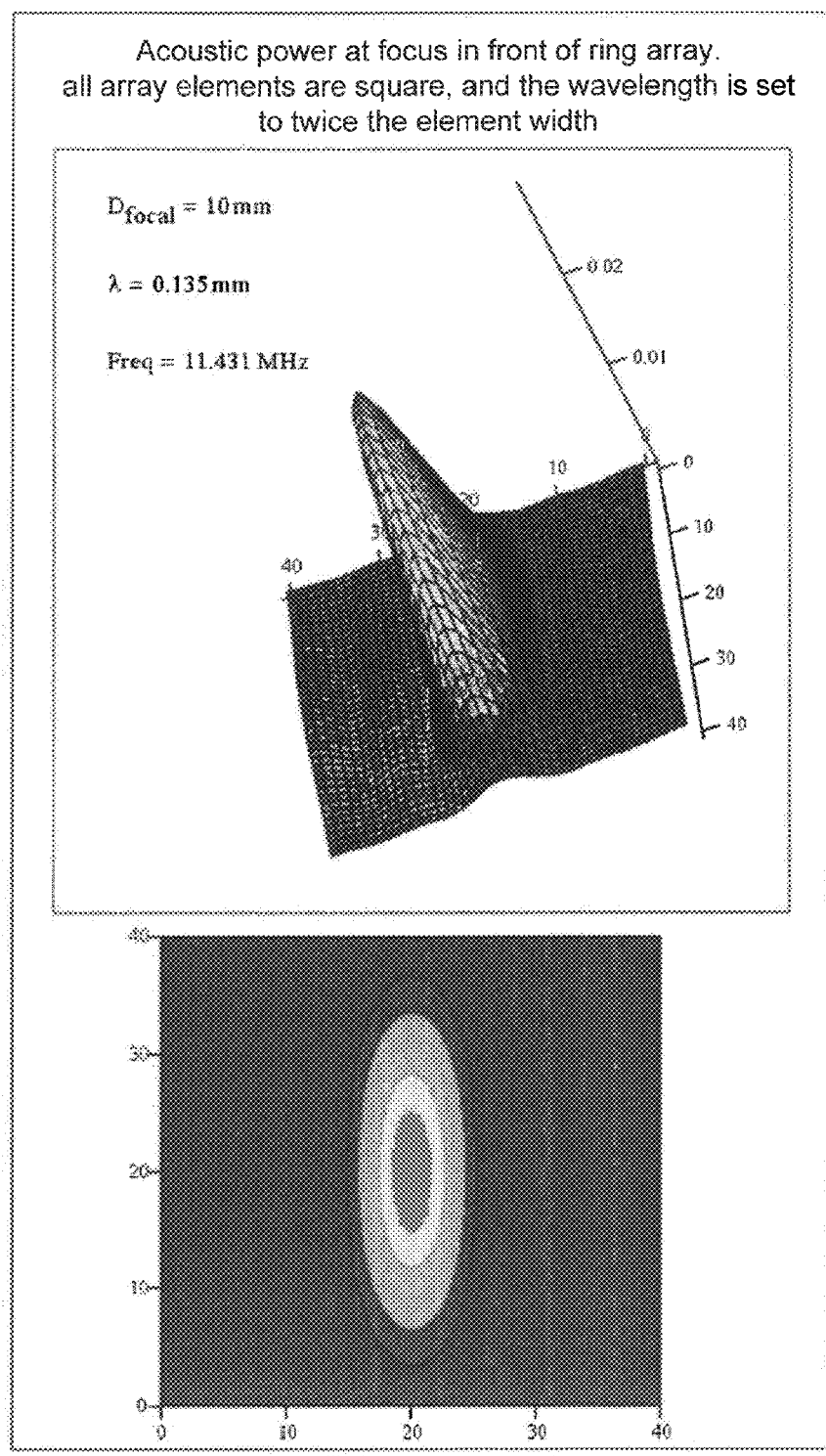
FIG. 10c is a three-dimensional presentation of the acoustic power, along with a top-down view.

Finally, it is useful to examine the case where the focused spot is further away, at d=1 cm. Now L=7.375 mm with 120 circumference elements and the spot size is 366 microns in the circumference direction. The axial spot size with 32 elements is 1250 microns. These results are confirmed by the Mathcad simulations of FIGS. 10a-10c, which gives a circumference spot size of 364 microns and an axial spot size of 1300 microns. Four such arrays can be "fired" at a time spaced equally around the capsule for p=4. So four acoustic image voxels can be acquired in one transmit pulse period. Repeating the calculations above for this yields $t_a$=15.8 usec, which establishes the maximum voxel acquisition rate of $R_{voxel}$=0.25 M voxels/sec and $t_{scan}$=2 msec, providing for a scan rate of 494 scans/sec where each scan is comprised of 512 circumference voxels. During one scan the capsule moves 0.08 of a spot size in the axial direction at the maximum peristalsis rate of 2 inches/sec. The resulting voxel overlap between scans allows for image stitching to provide a continuous scanned image. Note that the above translates the array one transducer element center-to-center distance, or 67.5 microns, around the circumference for the next transmit pulse and echo receive cycle, which is 0.3 of the spot size for the circumference array. If the array is translated two transducer elements between cycles, or a 0.6 of a circumference spot size, then the scan rate doubles with the same data output rate, and the capsule then moves 0.04 of a spot size in the axial direction between scans, for greater voxel overlap, which enables post image processing that could increase effective resolution by at least a factor of two. Conversely, the scan rate can be kept the same to halve the data rate, which could be an important data bandwidth consideration.

Timing Considerations:

The timing of individual transducer elements in the array needs to be theoretically exact to provide for a converging acoustic signal wave front at the image point. For the acoustic signals from each transducer element to arrive at the focused spot simultaneously, the array elements are fired in order of their distance away from the array center, with the corner elements of the array firing first, and the center ones last. For the d=1 mm example above, the corner elements will need to be fired 0.644 usec before the center ones. The timing difference between adjacent transducer elements at and near the array edge is around 61 nsec. For elements closer to the center, the difference of acoustic travel distances becomes on the order of 0.5 $D^2$/d between transducer elements, which for this case is 2.2 micron, or 1.5 nsec, which would require a clock frequency on the order of 670 MHz to drive a timing counter. The ratio of 0.644 usec/1.5 nsec is 429, which would require a 9-stage timing counter.

For the d=5 mm example above, the corner elements will need to fire 1.1 usec before the center ones. The timing difference between adjacent transducer elements at and near the array edge is around 114 nsec. For those at or near the center the timing difference between adjacent elements is about 0.3 nsec, which would require a clock frequency of 3.4 GHz to drive a timing counter. The ratio of 1.1 usec/0.3 nsec is 3367, requiring a 12-stage timing counter to accommodate.

An upper bound for the timing difference between corner elements and the center is for d becoming much larger than r, for which the array encompasses one third of the capsule circumference, and the difference in distance traveled to the focused spot becomes just ½ r. In this case ½ r, =2.75 mm, for an upper limit of 1.875 usec for when the corner elements need to fire before the center ones.

There is a difference in what is theoretically required for the timing of transducer array elements and what can be practically achieved. So it is necessary to examine how timing errors between transducer elements affects array performance. Mathcad simulations were performed with phase shifted signals from the transducer elements to examine spot size vs array size, versus resolution of both phase and amplitude. The simulations showed excellent spot focus results for 1-bit resolution of the phase and 2-bits for the amplitude, as shown in FIGS. 8, 9 and 10. So two-bit resolution in the phase shift would then be more than adequate. This provides a $\lambda$/4=33.75 micron phase resolution, which is equivalent to a time resolution of about 22 nsec for a clock speed of 45 MHz. As discussed above, the maximum counter length is 1.875 usec, for a dynamic range of 1.875 usec/22 nsec=85, requiring a 7 stage counter. Other design selections would fall under the scope of this invention.

The transmit array counter will operate only when the transmit array is active. For the d=0.5 cm example above, the counter is active for 1.1 usec, and for d=0.1 cm, 0.64 usec. The total data acquisition times are 8.87 and 2.76 usec respectively, providing counter duty cycles of 12.4 and 23.2% respectively. As will be discussed in a later section, this same counter may also be employed as a timer for the receive signal.

Array Size Considerations:

The focused array sizes around the circumference used in the above examples are limited by capsule curvature. As seen for the d=1 mm example, the resulting array provided an f-number of 0.4, which is less than is practically achievable. This provides for the possibility of reducing the array size to achieve an f-number that is more practically achievable. For example, an f-number=1 would be obtained with an array the size of L=$l_f$, yielding an array size of L=1 mm. More of this smaller array can be placed around the capsule, increasing scan rate. Also, the timing with the corner elements is faster, which further increases the scan rate. The disadvantage is that actual spot size will increase. This may be offset by the greater voxel overlap that increased scan rate with larger spot size will provide, allowing image processing techniques to recover enhanced resolution. Capsule curvature will limit the target achievability of L=$l_f$ as d increases. For d greater than 6.5 mm the array size will be limited by capsule curvature and the f-number will become greater than one.

As the capsule moves through the intestinal tract, it will be in positions where the distance, d, from the surface to the intestinal wall varies around the circumference. This situation will require dynamic array size configuration around the circumference as positions change. For example, d may vary from 1 mm on one side of the capsule to 5 mm on the other side. So as the array is stepped around the circumference as described above, the array size will vary to accommodate the changing value of d. The scan rate will also vary to accommodate the changing timing conditions of the array size. Stepping distance can also vary, as described above, to increase scan rate to maintain the desired amount of voxel overlap in the axial direction. This dynamic array environment will be directed by a central controller, which controls all aspects of array timing and size.

Receiver Issues:

As discussed above, in a typical medical ultrasound scanner, once the timing is established for the transmit elements, the same timing is used for the receive elements to minimize image artifacts. Because of the complications of implementing that approach on a capsule platform, a simpler method is proposed, where only a block of transducer elements in the center of the array are is used as the receiver. To insure adequate phase coherence the block dimension is determined by the edge elements having a distance difference to the spot of no more than $\lambda$/10 than the center elements, which will ensure at least 95% constructive interference for the elements. For d=1 mm this constrains the block size to 311 microns on a side in the longitudinal direction, which accommodate 4.6 transducer elements, which is rounded down to 4. Around the circumference, the curvature also needs to be considered, and the array size is limited to 264 microns, which can accommodate 3.9 transducer elements, which is rounded up to 4. Therefore, the receive array contains a total of 16 transducer elements. The considerations for the number of receive array elements are by way of example only, and other considerations could yield a different number of receive array elements and still fall under the scope of the invention.

The receive array is configured as soon as the signal transmission cycle is completed and the signal oscillations are dampened. Upon the last transducer element transmission, which will be from the center-most elements, a clock timer is initiated, and the receive array starts listening for the echo signal from the intestinal wall tissue, distance d away from the array. The echo time will be that required for the acoustic signal to travel the round trip distance of 2 d. For d=1 mm, this is 1.3 usec. If a distance resolution is desired equivalent to the depth of focus, 45 microns for this case, then the minimum timer increment would need to be 30 nsec, requiring the counter to be clocked at 34 MHz. A 6-stage counter would accommodate this count range. These range of numbers allow the same counter as used for the transmit array timing to be used for receive array timing. When the echo signal is detected, the counter downloads the count into a register for transmission to the external data receiver. Multiple echo detection would require a smaller time increment and a resultant higher clock rate for the counter.

Transmit and Receive Array Operation:

The distance, d, of the focused spot on the intestinal wall to the array determines the optimal size and timing for both transmit and receive arrays. Since there is voxel overlap between scans, the previously measured value of d can be used to set up the array values for the next scan at the same location. This can be accomplished either through calculations or look up tables, or a combination of both. These values are then pre-loaded for immediate availability for the next scan. These array values would need to be stored in memory for each of the 512 voxel locations around the capsule circumference. For the d=1 mm case above, there are 36×32=288 transducer elements in each array quadrant, so 512×288=–147,456 timing data points would need to be stored for the transmission arrays. An upper limit would be for large values of d where the effective array size is limited to one third of the circumference of the capsule, which would have a total of 170×32=5,440 elements, for 1,360 in each quadrant. Than the number of timing points to be stored is 696,320.

For the first scan, there is no previously measured value of d, and capsule would go into "discover" mode for the first accurate measurement. One approach is to start with the minimum d value and step upward until an echo signal is received of the expected magnitude. This measured value of d would then be used for the next measurement at that location to hone in on and lock onto an accurate value.

The above discusses many design parameters that need to be optimized for the USCE. The choices for the design parameters selected above are by way of example only, and other choices would fall under the scope of the invention. Additionally, the concepts may be applied to formats other than a capsule, such as for endoscopes and catheters, for example.

CONCLUSION

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present invention in any way.

What is claimed is:

1. An ultrasound scanning capsule endoscope, comprising:
    a housing having a size that is ingestible; and
    an ultrasonic transducer array, wrapped around a circumference of the housing, configured to transmit a plurality of ultrasonic signals and to receive a plurality of echo signals,
    wherein wavelengths of the plurality of ultrasonic signals are configured to be a multiple of a center-to-center transducer element spacing between adjacent transducers in the ultrasonic transducer array; and
    wherein the ultrasonic transducer array is further configured to:
        determine a distance between the ultrasound scanning capsule endoscope and an intestinal wall of an animal, and
        dynamically vary, based upon the distance, a number of transducer elements of the ultrasonic transducer array used to transmit the plurality of ultrasonic signals.

2. The ultrasound scanning capsule endoscope of claim 1, wherein the number of transducers is greater than a second number of transducers configured to receive the plurality of echo signals.

3. The ultrasound scanning capsule endoscope of claim 1, wherein the wavelengths are integer multiples of the center-to-center transducer element spacing.

4. The ultrasound scanning capsule endoscope of claim 1, wherein the ultrasonic transducer array is configured to enter into a receive mode of operation to receive the plurality of echo signals after transmitting the plurality of ultrasonic signals in a transmit mode of operation.

5. The ultrasound scanning capsule endoscope of claim 1, wherein a first group of transducers in the ultrasonic transducer array that is further away from a center of the ultrasonic transducer array is configured to provide respective ultrasonic signals from among the plurality of ultrasonic signals before a second group of transducers in the ultrasonic transducer array that are closer to the center.

6. The ultrasound scanning capsule endoscope of claim 1, wherein the ultrasonic transducer array is configured and arranged to form a plurality of quadrants around the circumference, each of the plurality of quadrants being configured to simultaneously image one or more voxels at a time around the circumference.

7. The ultrasound scanning capsule endoscope of claim 6, wherein each of the plurality of quadrants is further configured to sequentially image the one or more voxels until all circumference voxels have been imaged.

8. The ultrasound scanning capsule endoscope of claim 1, further configured to vary a scan rate of the ultrasonic transducer array with a change in the position of the ultrasound scanning capsule endoscope.

9. The ultrasound scanning capsule endoscope of claim 1, wherein the ultrasonic transducer array is configured to adjust the number of the transducer elements of the ultrasonic transducer array until the transducer elements receive an echo signal from among the plurality of echo signals in response to transmission of an ultrasonic signal from among the plurality ultrasonic signals.

10. The ultrasound scanning capsule endoscope of claim 1, wherein the ultrasonic transducer array is configured to determine the distance by echo detection.

11. An ultrasound scanning capsule endoscope, comprising:
    an ultrasonic transducer phased array wrapped around a circumference of a housing configured to transmit an ultrasonic signal and to receive an echo signal;
    wherein a wavelength of the ultrasonic signal is a multiple of a center-to-center transducer element spacing between adjacent transducers in the ultrasonic phased transducer array; and
    wherein the ultrasonic transducer phased array is further configured to:
        determine a distance between the ultrasound scanning capsule endoscope and an intestinal wall of an animal, and
        dynamically vary, based upon the distance, a number of transducers in the ultrasonic transducer phased array used to transmit the ultrasonic signal.

12. The ultrasound scanning capsule endoscope of claim 11, wherein the number of transducers is greater than a second number of transducers configured to receive the echo signal.

13. The ultrasound scanning capsule endoscope of claim 12, wherein the wavelength is an integer multiple of the center-to-center transducer element spacing.

14. The ultrasound scanning capsule endoscope of claim 11, wherein the ultrasonic transducer phased array is configured to enter into a receive mode of operation to listen for the echo signal after transmitting the ultrasonic signal in a transmit mode of operation.

15. The ultrasound scanning capsule endoscope of claim 11, wherein transducers in the ultrasonic transducer phased array that are further away from a center of their respective phased array provide the ultrasonic signal before transducers in the ultrasonic transducer phased array that are closer to the center.

16. The ultrasound scanning capsule endoscope of claim 11, wherein the ultrasonic transducer phased array is configured and arranged to form a plurality of quadrants around the circumference, each of the plurality of quadrants being configured to simultaneously image one or more voxels at a time around the circumference.

17. The ultrasound scanning capsule endoscope of claim 16, wherein each of the plurality of quadrants is further configured to sequentially image the one or more voxels until all circumference voxels have been imaged.

18. The ultrasound scanning capsule endoscope of claim 11, further configured to vary a scan rate of the ultrasonic transducer phased array with a change in the position of the ultrasound scanning capsule endoscope.

19. The ultrasound scanning capsule endoscope of claim 11, wherein the ultrasonic transducer phased array is configured to adjust the number of the transducer elements of the ultrasonic transducer phased array until the transducer elements receive the echo signal in response to transmission of the ultrasonic signal.

20. The ultrasound scanning capsule endoscope of claim 11, wherein the ultrasonic transducer phased array is configured to determine the distance by echo detection.

21. A method, comprising:
    determining a distance between an ultrasound scanning capsule endoscope and an intestinal wall of an animal;
    dynamically varying, based upon the distance, a first number of transducers in an ultrasonic transducer array wrapped around a circumference of a housing of the ultrasound scanning capsule endoscope that are used to transmit an ultrasonic signal;
    transmitting, by the first number of transducers, the ultrasonic signal having a wavelength that is a multiple of a center-to-center transducer element spacing between adjacent transducers in the ultrasonic transducer array; and
    receiving, by the ultrasonic transducer array, an echo signal.

22. The method of claim 21, wherein the receiving comprises:
    receiving, by a second number of transducers in the ultrasonic transducer array, the echo signal, the second number of transducers being less than the first number of transducers.

23. The method of claim 21, wherein the transmitting comprises:
    transmitting by transducers in the ultrasonic transducer array that are further away from a center of the ultrasonic transducer array provide the ultrasonic signal before transducers in the ultrasonic transducer phased array that are closer to the center.

24. The method of claim 21, further comprising varying a scan rate of the ultrasonic transducer array with a change in the position of the ultrasound scanning capsule endoscope.

25. The method of claim 21, wherein the dynamically varying comprises:
    adjusting the number of the transducer elements until the transducer elements receives the echo signal in response to transmission the ultrasonic signal.

26. The method of claim 21, wherein the determining comprises:
    determining the distance by echo detection.

* * * * *